US007656157B2

(12) United States Patent
Smith et al.

(10) Patent No.: US 7,656,157 B2
(45) Date of Patent: Feb. 2, 2010

(54) METHOD FOR IMPROVING THE PRECISION OF TIME DOMAIN LOW FIELD H-NMR ANALYSIS

(75) Inventors: Thomas Riddel Smith, Richmond, TX (US); Pierre Nazareth Tutunjian, Houston, TX (US)

(73) Assignee: Shell Oil Company, Houston, TX (US)

( * ) Notice: Subject to any disclaimer, the term of this patent is extended or adjusted under 35 U.S.C. 154(b) by 66 days.

(21) Appl. No.: 11/834,519

(22) Filed: Aug. 6, 2007

(65) Prior Publication Data

US 2008/0036461 A1 Feb. 14, 2008

Related U.S. Application Data

(60) Provisional application No. 60/821,792, filed on Aug. 8, 2006.

(51) Int. Cl.
*G01V 3/00* (2006.01)

(52) U.S. Cl. ....................................... 324/311; 324/309

(58) Field of Classification Search ......... 324/300–322; 600/407–445
See application file for complete search history.

(56) References Cited

U.S. PATENT DOCUMENTS

| | | | | |
|---|---|---|---|---|
| 4,453,147 | A | 6/1984 | Froncisz et al. | 333/219 |
| 5,184,078 | A | 2/1993 | Rapoport | 324/321 |
| 5,194,811 | A | 3/1993 | Murphy-Boesch et al. | 324/322 |
| 5,212,450 | A | 5/1993 | Murphy-Boesch et al. | 324/322 |
| 5,258,710 | A | 11/1993 | Black et al. | 324/309 |
| 5,371,464 | A | 12/1994 | Rapoport | 324/306 |
| 5,424,644 | A | 6/1995 | Zeiger | 324/318 |
| 5,886,525 | A * | 3/1999 | Yesinowski et al. | 324/321 |
| 6,583,622 | B1 | 6/2003 | Hills | 324/307 |
| 6,941,018 | B2 | 9/2005 | Ohishi et al. | 382/218 |
| 6,984,980 | B2 | 1/2006 | Kruspe et al. | 324/303 |
| 7,199,581 | B2 * | 4/2007 | Corver et al. | 324/308 |
| 7,352,179 | B2 * | 4/2008 | Chen et al. | 324/303 |
| 2008/0174309 | A1 * | 7/2008 | Pusiol et al. | 324/306 |
| 2009/0146658 | A1 * | 6/2009 | McDowell et al. | 324/309 |
| 2009/0149736 | A1 * | 6/2009 | Skidmore et al. | 600/421 |

FOREIGN PATENT DOCUMENTS

| | | |
|---|---|---|
| DE | 102004050737 | 4/2006 |
| WO | WO03102615 | 12/2003 |
| WO | WO2004104600 A2 | 12/2004 |

OTHER PUBLICATIONS

V. Rutar, "Magic Angle Sample Spinning NMR Spectroscopy of Liquids as a Nondestructive Method for Studies of Plant Seeds," *J. Agric. Food Chem.* 1989, vol. 37 pp. 67-70, XP002462631.

(Continued)

*Primary Examiner*—Brij B Shrivastav

(57) ABSTRACT

A method for improving the precision of time domain low field H-NMR analysis, the method comprising rotating a sample within a RF coil and acquiring multiple time domain signals for the sample at multiple orientations within the RF coil.

12 Claims, 2 Drawing Sheets

OTHER PUBLICATIONS

Harald Todt et al., "Water/Moisture and Fat Analysis by Time-Domain NMR," Food Chemistry, Elsevier Science Publisher Ltd., GB, vol. 96, No. 3, Jun. 2006, pp. 436-440, XP005188604.

ASTM D4808, "Standard Test Methods for Hydrogen Content of Light Distillates, Middle Distillates, GAs Oils, and Residua by Low-Resolution Nuclear Magnetic Resonance Spectroscopy", 1988.

ASTM D3701, "Standard Test Method for Hydrogen Content of Aviation Turbine Fuels by Low Resolution Nuclear Magnetic Resonance Spectrometry", 1978.

ASTM D5292, "Standard Test Method for Aromatic Carbon Contents of Hydrocarbon Oils by High Resolution Nuclear Magnetic Resonance Spectroscopy", 1992.

* cited by examiner

METHOD FOR IMPROVING THE PRECISION OF TIME DOMAIN LOW FIELD H-NMR ANALYSIS

This application claims the benefit of U.S. provisional application No. 60/821,792 filed Aug. 8, 2006.

FIELD OF THE INVENTION

The present application is directed to a method for improving the precision of time domain low field H-NMR analysis.

BACKGROUND OF THE INVENTION

Time domain low field H-NMR analysis determines the quantity of hydrogen in a sample. In a typical time domain low field H-NMR analysis, a sample is inserted into a H-NMR instrument and subjected to a static polarizing magnetic field and to one or more radio frequency (RF) fields that are generated by a RF coil. The period of RF excitation typically lasts several microseconds and is known as the RF pulse. Following the RF pulse, a H-NMR signal is acquired. The H-NMR signal is generated in the RF coil. The hydrogen content of the sample is determined by comparing the intensity of the acquired H-NMR signal to a signal from one or more standards.

Typically, multiple scans for a given sample are acquired and co-averaged to improve signal to noise. The delay between acquired scans is known as the relaxation delay time and is on the order of several seconds. Ideally, one would acquire the first data point following the RF pulse from the H-NMR signal. However, it is typical to acquire data over a small sampling window, known as the data acquisition window.

U.S. Pat. No. 4,701,705 describes a low field H-NMR apparatus for conducting NMR moisture measurements. In the apparatus, a NMR apparatus 15 cooperates with a static pipe 12 or other belt or conveyer system. A flowing material passes along the static pipe. A pulse is transmitted to the coil from the NMR apparatus 15 and an output is formed which is the transient NMR response. The output signal is applied to a peak signal detector 20. The peak signal detector and the output signal are both input to a CPU 22. The output signal is first passed through a digitizer 24 which converts the analog signal into a series of digital words. The CPU collaborates with a memory 26, and periodically forms an output which is an indication of moisture. The indicator 28 provides data which typically is expressed in the form of percentage moisture content.

In FIG. 2 of U.S. Pat. No. 4,701,705, the ordinate is the transient NMR response measured in volts. Several curves extend through about 50 microseconds. A peak first occurs (at about 5 to 7 microseconds on the graph) and decay is thereafter noted. U.S. Pat. No. 4,701,705 does not describe a method for minimizing inaccuracies which may result from assymmetry of the sample flowing through the pipe 12.

Some patents describe rotating a sample about an axis that is subtantially perpendicular to the direction of the magnetic field in the gap. For example, U.S. Pat. No. 5,184,078 describes the use of an O-ring to couple the test tube to a motor. The motor can then be controlled to rotate the test tube at a desired speed. However, the system described in U.S. Pat. No. 5,184,078 is used to perform high field NMR. See col. 4, 11. 47-col. 5, 1. 10.

A sample is spun during high field NMR in order to reduce the effect of the inherent inhomogeneity in the static magnetic field to which the sample is exposed. In solid state high field NMR analysis, the sample also is spun in order to reduce or eliminate the effects of the inherent anisotropies of internal magnetic interactions which are typically averaged out in liquids but contribute to severe loss of spectral resolution in solids. The data acquired during sample spinning is then Fourier transformed to produce highly resolved peaks. The higher the peak resolution, the more accurate and complete is the identification and quantification of chemical structures present in the sample.

In high field NMR, the spinning period typically is shorter than the data acquisition window. In other words, the sample undergoes many rotations over the typical data acquisition window. So, in high field NMR the spinning is done in such a way as to allow all parts of the sample to experience many different orientations within the data acquisition window in such a way that all parts of the sample experience, on average, the same local field. One thus obtains NMR spectra with optimally narrowed lineshapes.

Low field NMR is not concerned with lineshapes because it does not involve a frequency domain spectrum and does not attempt to resolve spectral features. Methods are needed to improving the precision of hydrogen content determination when using time domain low field H-NMR analysis.

SUMMARY OF THE INVENTION

Figure 1:
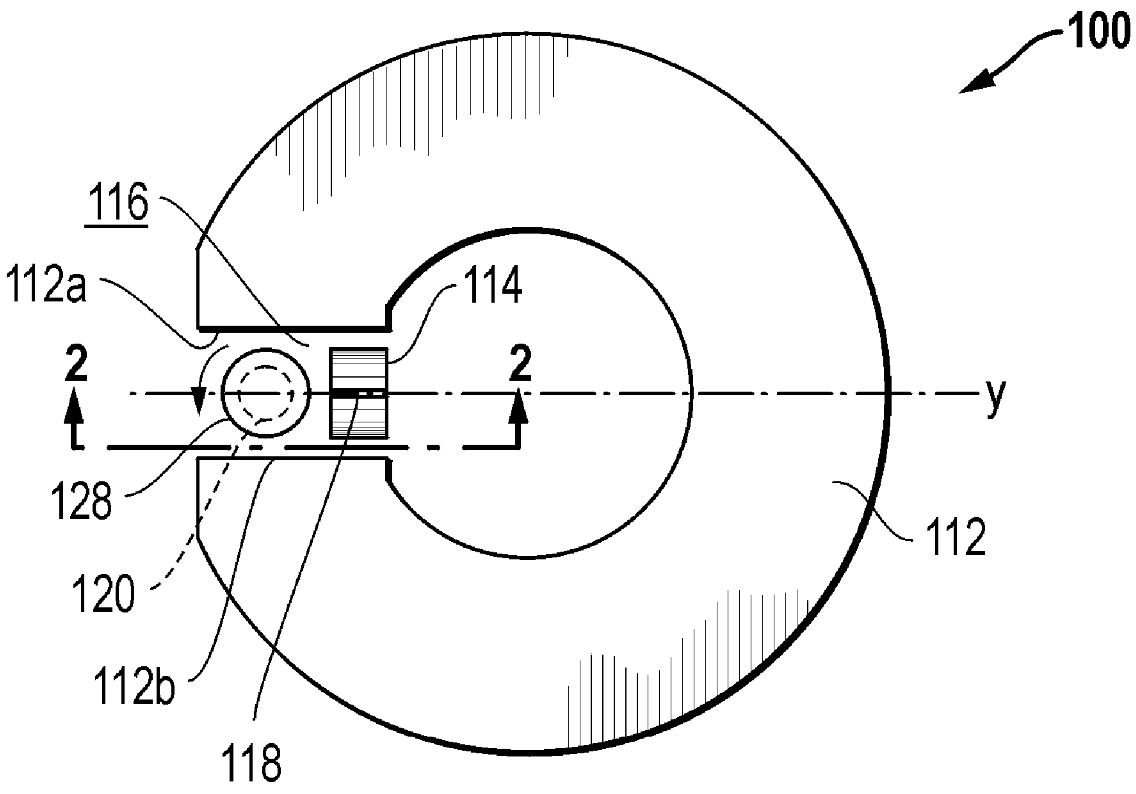
FIG. 1 is a simplified top view of an H-NMR spectroscopy instrument.

The present application provides a method for improving the precision of time domain low field H-NMR analysis, the method comprising rotating a sample within a RF coil and acquiring multiple time domain signals for the sample at multiple orientations within the RF coil.

The present application also provides a method for improving the precision of time domain low field H-NMR analysis, the method comprising rotating a sample within a RF coil while continuously acquiring multiple time domain signals for the sample at multiple orientations within the RF coil.

In one embodiment, the application provides a method for improving the precision of time domain low field H-NMR analysis, the method comprising: rotating a sample within the RF coil at a rotation rate of 1° or less per data acquisition window while continuously acquiring multiple time domain signals for the sample at multiple orientations within the RF coil.

In one embodiment, the application provides a method for improving the precision of time domain low field H-NMR analysis, the method comprising: rotating a sample within a RF coil at a rotation rate of about 15 revolutions per minute while continuously acquiring multiple time domain signals for the sample over data acquisition windows having a duration of about 40 μsecs.

DETAILED DESCRIPTION OF THE INVENTION

Some time domain low field H-NMR instruments use RF coil designs with inherent axial asymmetry. An example is a loop gap RF coil. The use of an inherently asymmetric RF coil minimizes variations in tuning from sample to sample. However, if the sample has a non-uniform proton density and/or if the sample is positioned slightly off center inside the RF coil, the inherently asymmetric RF coil also may produce H-NMR signals for the same sample which have different intensities at different sample orientations in the RF coil.

A sample may have an inherently asymmetric hydrogen density for a number of reasons. For example, the sample tube may vary in size, shape, and/or wall thickness along its length and/or its diameter. The tube may be placed slightly off axis inside the RF coil. The sample itself may have a non-uniform hydrogen content. An example would be if the sample is a solid or a heterogeneous emulsion. The sample may also be subject to a temperature gradient.

The present application provides a method for improving the precision of time domain low field H-NMR analysis comprising rotating a sample within a RF coil and acquiring multiple time domain signals for the sample at multiple orientations within the RF coil. In one embodiment, one or more standards also are rotated within the RF coil and multiple time domain signals are acquired for the one or more standards at multiple orientations within the RF coil.

The multiple time domain signals for the sample and for the one or more standards, respectively, are co-added and averaged, producing an average time domain signal for the sample and an average time domain signal for the one or more standards. The hydrogen content of the sample is determined by comparing the intensity of the average time domain signal for the sample with the intensity of the average time domain signal for the one or more standards. The method improves the precision and ultimately the accuracy of the hydrogen content determination for the sample. The improvement is particularly evident where the hydrogen distribution in the sample is inherently asymmetric. The hydrogen distribution in the sample may be inherently asymmetric, for example, where the sample is positioned slightly off center, and/or where the sample is subjected to a temperature gradient which causes a non-axially symmetric magnetization profile.

The reason for rotating the sample during time domain low field H-NMR analysis is different from the reason for sample spinning at high speeds using high field NMR instruments. As explained above, in liquid state high field NMR analysis, the sample is spun in order to reduce the effect of the inherent inhomogeneity in the static magnetic field to which the sample is exposed. In solid state high field NMR analysis, the sample also is spun in order to reduce or eliminate the effects of the inherent anisotropies of internal magnetic interactions which are typically averaged out in liquids but contribute to severe loss of spectral resolution in solids. The data acquired during sample spinning is then Fourier transformed to produce highly resolved peaks. The higher the peak resolution, the more accurate and complete is the identification and quantification of chemical structures present in the sample.

In contrast, the reason for rotating the sample during time domain low field H-NMR analysis is to minimize signal intensity variations due to inherent asymmetries in RF coil design. The more repeatable and precise the intensity of the H-NMR time domain signal, the more accurate the ultimate hydrogen content determination following proper calibration against known standards.

The H-NMR signals are acquired over a period of time called the data acquisition window. In high field NMR, the spinning period typically is shorter than the data acquisition window. In other words, the sample undergoes many rotations over the typical data acquisition window. So, in high field NMR the spinning is done in such a way as to allow all parts of the sample to experience many different orientations within the data acquisition window in such a way that all parts of the sample experience, on average, the same local field. One thus obtains NMR spectra with optimally narrowed lineshapes.

In low field time domain H-NMR, the rotation period is longer than the data acquisition window. In other words, the sample does not rotate significantly during the data acquisition window. The low rate of rotation avoids fluctuation in the H-NMR signal as data is acquired during the data acquisition window. Low field NMR is not concerned with lineshapes because it does not involve a frequency domain spectrum and does not attempt to resolve spectral features.

Low field H-NMR attempts to minimize the dependence of the time domain total hydrogen signal on sample orientation. The need to minimize such dependence arises from RF coil asymmetric design coupled with sample asymmetric proton distribution and/or slight off centering of the vial in the RF probe. In low field H-NMR, the rotation is very slow so that the sample barely reorients itself during the data acquisition window. This guarantees that the time domain signal acquired during the data acquisition window is constant albeit different for different orientations. Co-adding and averaging the time domain signals from different orientations minimizes orientational effects.

In quantitative terms, if "AT" is the data acquisition window, or time, and "P" is the period of the applied rotation, then the following equation applies:

$$360 \cdot AT/P \leqq 1°$$

Where AT equals 40 microseconds, the period P of the motion is greater than or equal to 0.0144 sec and the spinning rate (1/P) is equal to or less than 4167 RPM (revolutions per minute). In one embodiment, the spinning rate is less than 4167 RPM.

In one embodiment, the rotation rate and the data acquisition window are controlled to produce a rotation of 1° or less per data acquisition window. In an advantageous embodiment, the rotation rate and the data acquisition window produce a rotation of 0.1° or less per data acquisition window. In an advantageous embodiment, the rotation rate and the data acquisition window produce a rotation of 0.01° or less per data acquisition window.

In one embodiment, the rotation rate is about 20 revolutions per minute (RPM) or less. In one embodiment, the rotation rate is about 17 revolutions per minute (RPM) or less. In one embodiment, the rotation rate is about 15 revolutions per minute (RPM) or less. In one embodiment, the rotation rate is about 5 revolutions per minute (RPM) or more. In one embodiment, the rotation rate is about 10 revolutions per minute (RPM) or more. In one embodiment, the rotation rate is about 12 revolutions per minute (RPM) or more. In one embodiment, the rotation rate is about 15 revolutions per minute (RPM).

In order to improve the signal to noise ratio, and to reduce variations associated with orientational effects due to asymmetric coil response, it is advantageous to average multiple time domain signals for multiple orientations. The number of scans taken is not critical, and substantially any suitable number of scans may be taken as long as signal to noise ratio is acceptable. Typically, from about 10 to about 20 time domain signals are acquired per sample. In one embodiment, about 16 time domain signals are acquired per sample using a data acquisition window of about 40 μsec with a delay of about 25 seconds between scans. In this embodiment, the total experimental time per sample is 400 sec.

In an advantageous embodiment, the sample is continuously rotated at about 15 rpm, and the duration of the data acquisition window is about 40 μsec with a delay of about 25 seconds between scans. In this embodiment, about 1/100, $000^{th}$ (0.00001 or $1\times10^{-5}$) of a revolution occurs during the data acquisition window.

The sample is rotated in the RF coil using any suitable method. The sample may be manually placed in the RF coil at multiple orientations and H-NMR signals acquired at each orientation. The sample also may be mechanically rotated to multiple orientations and H-NMR signals acquired at multiple orientations during the rotation.

In an advantageous embodiment, a low field time domain H-NMR instrument is associated with an energy source to provide continuous, relatively low RPM rotation of the sample in the RF coil. Any suitable energy source may be used to rotate the sample. For example, a suitable energy source is a low RPM motor.

In the examples, the shaft of a Pittman model GM9413G607 with 65.5:1 gear ratio operated at 5V DC was mechanically associated with sample vials in a Bruker Minispec MQ20 NMR Analyzer obtained from Bruker Optics, Inc.

Figure 2A:
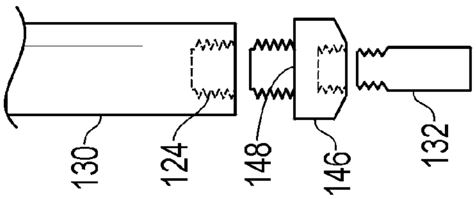
FIG. 2A is a blow-up detail of a distal end of a sample holder assembly.
Figure 2:
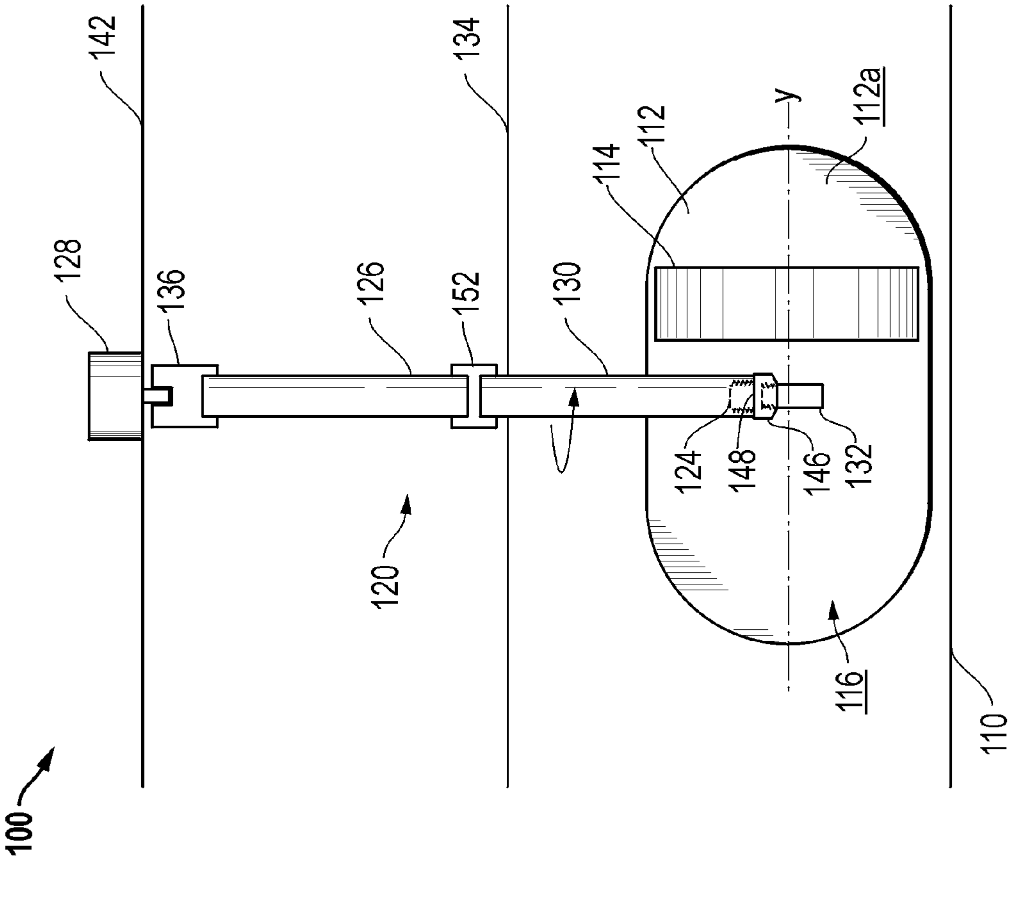
FIG. 2 is a vertical cross-sectional view through line 2-2 in FIG. 1.

The simplified illustrations of FIGS. 1, 2, and 2A depict one embodiment of an H-NMR spectroscopy instrument (spectrometer) 100 that is operable to implement the sample rotation required by the present low field H-NMR method. In this particular embodiment, the H-NMR spectroscopy instrument 100 is a commercially available model that has been modified to provide sample rotation capability. The H-NMR instrument 100, and the modifications provided thereto, illustrate structure suitable for use with previously described low field NMR method(s). Other commercially available H-NMR instrument designs (that employ an inherently axially symmetric RF coil) may be more or less amenable to the same type of structural modifications. One type of H-NMR spectroscopy instrument suitable for the modification described herein is a Bruker Minispec MQ20 NMR Analyzer obtained from Bruker Optics, Inc. The desired structure also may be provided as an original construction or design, rather than a modification to an existing H-NMR instrument.

For present purposes, the basic representation of an H-NMR spectroscopy instrument 100 in FIGS. 1 and 2 is shown having a housing 110, a permanent magnet 112 supported in the housing 110 and a radio frequency (RF) coil 114 supported in the housing 110 proximate the permanent magnet 112. The permanent magnet 112 is generally circular and includes two vertical faces 112*a*, 112*b* that define a gap 116 therebetween. The permanent magnet 112 generates a static magnetic field in the area of the gap 116 and in a direction from one face to the other face. The RF coil 114 is situated near one end of the gap 116 and aligned about a longitudinal Y-axis that extends generally centrally through the gap 116 and the RF coil 114. As is known in the H-NMR measurement art, the RF coil 114 is operable to send excitation pulses into the gap 116 such that, when a sample is placed in the gap 116 in the presence of the static magnetic field, it generates an oscillating magnetic field having a direction that is perpendicular to the static magnetic field. The RF coil 114 also has the capability of receiving the resultant H-NMR signals from the sample. Thus, the gap 116 serves as a measurement region or sample field 116 of the H-NMR instrument 100.

The RF coil 114 represented in FIGS. 1 and 2 typically is provided as one part of an assembly of hardware or a sample probe. The assembly or probe may include other coils, circuitry for RF generation, circuitry for signal output and processing, and other components, the details of which are not necessary for the present description.

As previously described, the present low field H-NMR method is particularly directed to H-NMR measurement techniques that employ RF coils which are inherently axially asymmetric. These include RF coils such as the loop gap resonator 114 depicted in FIG. 1. The loop gap resonator 114 may be cylindrical or disc shaped, and is situated vertically with its centerline in alignment with longitudinal Y-axis. The loop gap resonator 114 includes a capacitor gap 118 that breaks the structural symmetry. The loop gap resonator 114 is, therefore, disposed facing the sample field 116 and operable to generate an oscillating magnetic field generally having a direction parallel with the Y-axis and perpendicular to the static magnetic field.

Commercially available H-NMR instruments are typically equipped with a sampling tube that extends downward into the sample field and in front of the loop gap resonator (or other RF coil). The sample to be measured is held near the bottom of the sampling tube in front of and generally in alignment with the loop gap resonator. As already discussed, this measurement configuration will generally provide variations in the H-NMR signals received from the sample, due to the inherent axial asymmetry of the RF coil and/or the other reasons previously discussed.

In the present embodiment, the H-NMR spectroscopy instrument 100 is equipped with a sample holder assembly 120 that provides, in one respect, an advantageous replacement for the prior art sample tube. The sample holder assembly 120 includes a dual-section shaft having a first section 126 detachably coupled with a DC motor 128 and a second section 130 that retains a sample container 132, such as a sample vial. In one embodiment, the first section 126 is a wood shaft 126 that is sized to accommodate the distance between the motor 128 and a top wall 134 of the instrument housing 110 and to transmit torque provided by the motor 128. A top or proximal end of the first section 126 is preferably detachably coupled to a shaft of the motor 128 by way of a flexible tubing connection 136 or the like. The second section 130 is preferably a plastic guide rod 130 that extends into the H-NMR housing 110. The guide rod 130 may be formed from any material having sufficient strength to handle torque and for supporting the sample container 132. The guide rod material is also advantageously a material that is not responsive or reactive to H-NMR measuring conditions. A flexible tube joint 152 is provided to couple the wood shaft 126 and guide rod 130 together, and provide for easy detachment of one section from the other section. Preferably, the joint 152 is positioned sufficiently clear of the top wall 134, so that the guide rod 130 can be readily uncoupled and be pulled from the housing 110 by handling a section of the rod 130 initially above the top wall 134.

Furthermore, it is preferred that the DC motor 128 is positioned well away from the housing 110, so that it is not affected by H-NMR measurement conditions. The DC motor 128 is, therefore, provided on a permanent support 142 well above the top wall 134. For the operation required by the present low-field H-NMR method, the DC motor may be of any design capable of low rotational speeds and continuous operation. It is further contemplated that any other suitable power source capable of providing the same automated operation may be used, if integration of such a power source can be done economically and efficiently.

Referring specifically to FIG. 2, and the detail view of FIG. 2A, the guide rod 130 extends downward into the H-NMR housing 110 and is equipped, at the distal end, with a threaded female connection 124. Further, the sample container 132 in this embodiment is equipped with a threaded cap 146 that is provided with a male threaded connector 148 for engagement with the female threaded connection 124 of the guide rod 130. The sample container 132 is thereby manually engageable with the guide rod 130 of the sample holder assembly 120.

In an operating mode, as shown in FIG. 2, the sample container 132 is secured to the distal end of the guide rod 130. The sample container 132 is positioned centrally in the sample field 116 and preferably generally centered about the longitudinal Y-axis of the RF coil 114. In this way, the sample in the sample container 132 is generally aligned with the RF coil 114 and centered about the Y-axis. Such positioning is preferred, but as discussed herein, is not necessarily required by the present low-field H-NMR method. The DC motor 128 may be operated to continuously rotate the sample container 132 (through rotation of sample holder assembly 120) about this position in the sample field 116 at the desired rotational speed and so that a target sample in the sample container 132 is moved a complete range of orientations relative to the RF coil 114, in accordance with the present low-field NMR method. At completion of the measurement operation, the guide rod 130 is uncoupled from the wood shaft 126, and then the guide rod 130 is removed from the H-NMR instrument housing 110, with the sample container 132 intact. To access the measured sample, the sample container 132 is disengaged from the guide rod 130 and then, the cap 146 is removed from the sample container 132.

The method has the advantage that it is not necessary to spend thousands of dollars on equipment required to spin the sample at a very high rate, as is necessary in high field NMR analysis. Even if the low field NMR instrument is modified to provide rotation, the required rotation rate of the sample is very low. The motor or other actuator required to induce rotation is relatively inexpensive. As a result, the precision of the hydrogen content of the sample may be significantly improved with a minor and relatively low cost modification of a standard low field unit.

The invention will be better understood with reference to the following examples, which are illustrative only:

COMPARATIVE EXAMPLE

A vial filled with a heavy gas oil sample was mounted, off-axis, in the coil of a Bruker Minispec MQ20 NMR Analyzer. The vial was maintained off center in order to exaggerate the effects of the non-axial symmetry of the proton density inside the coil. The sample was manually placed in the coil at four different orientations (referred to as 0, 90, 180 and 270, in the table below). The data acquisition window was set at 40 μsec per scan and 16 scans were collected with a 25 second delay between successive scans. For each static "off-axis" orientation, the time domain signal at the various orientations, the time domain average, and the standard deviation and % standard deviation are shown below:

| Off Center Vial | NMR Signal |
|---|---|
| Location 0 | 13.6492 |
| Location 90 | 11.8655 |
| Location 180 | 14.0239 |
| Location 270 | 15.9404 |
| Average | 13.8698 |
| Standard Deviation | 1.6710 |
| % Standard Deviation | 12.0480 |

Relatively large variability in the NMR signals was seen depending upon the orientation of the sample in the instrument.

EXPERIMENTAL EXAMPLES

Example 1

The vial from the comparative example was run off-center four times under mechanical rotation using the Bruker analyzer connected to the shaft of the low RPM motor. The rotation rate was 15 revolutions per minute. Each run was initiated at a different starting orientation. The data acquisition window was set at 40 μsec per scan and 16 scans were collected with a 25 second delay between successive scans.

The rotation was slow compared to the data sampling window and thus the sample was essentially "static" during each scan. Over the 16 scans, the vial rotated roughly 100 revolutions. Time domain signals were acquired for four different starting positions of the sample. The results are shown in the following Table:

| Off Center Vial Rotated | NMR Signal |
|---|---|
| Rotation 1 | 13.9220 |
| Rotation 2 | 13.8273 |
| Rotation 3 | 14.0991 |
| Rotation 4 | 13.8481 |
| Average | 13.9241 |
| Standard Deviation | 0.1235 |
| % Standard Deviation | 0.8871 |

A significant improvement in the % Standard Deviation was seen even in the off center vial when the sample in the comparative example was rotated. Rotation of the off center sample decreased the standard deviation by roughly a factor of ten (from about 12% to 1%).

Example 2

A second sample-filled vial was properly centered in the RF coil at different orientations, designated "0, 90, 180, and 270." The results are shown in the following Table:

| On Center Vial Static | NMR Signal |
|---|---|
| Location 0 | 70.6312 |
| Location 90 | 70.6732 |
| Location 180 | 70.4163 |
| Location 270 | 70.7852 |
| Average | 70.6265 |
| Standard Deviation | 0.1545 |
| % Standard Deviation | 0.2187 |

Proper centering reduced the variability of the NMR signals, as seen by the % standard deviation of 0.2187. This was expected since proper on axis centering greatly reduces the asymmetry in the hydrogen distribution as viewed by the inherently non axially symmetric RF loop gap resonator coil.

Example 3

Example 2 was repeated, but the sample was rotated as in Example 1. The results are shown in the following Table:

| On Center Vial Rotated | NMR Signal |
|---|---|
| Rotation 1 | 70.6159 |
| Rotation 2 | 70.6435 |

-continued

| On Center Vial Rotated | NMR Signal |
|---|---|
| Rotation 3 | 70.6406 |
| Rotation 4 | 70.6543 |
| Average | 70.6386 |
| Standard Deviation | 0.0162 |
| % Standard Deviation | 0.0230 |

Rotation of the centered vial of Example 2 produced a factor of 10 improvement in % standard deviation.

Persons of ordinary skill in the art will recognize that many modifications may be made to the foregoing description. The embodiments described herein are meant to be illustrative only and should not be taken as limiting the invention, which will be defined in the claims.

We claim:

1. A method for improving the precision of time domain low field H-NMR analysis, the method comprising rotating a sample within a RF coil and acquiring multiple time domain signals for the sample at multiple orientations within the RF coil and averaging the multiple time domain signals for the sample, producing an average time domain signal for the sample;

rotating one or more standards within the RF coil, acquiring multiple time domain signals for the one or more standards at multiple orientations within the RF coil, and producing an average time domain signal for the one or more standards;

determining the hydrogen content of the sample by comparing the intensity of the average time domain signal for the sample to the intensity of the average time domain signal for the one or more standards.

2. The method of claim 1 wherein the multiple time domain signals have a percent standard deviation and rotating the sample within the RF coil produces a magnitude of about 10 or more reduction in the percent standard deviation.

3. A method for improving the precision of time domain low field H-NMR analysis, the method comprising rotating a sample within a RF coil while continuously acquiring multiple time domain signals for the sample at multiple orientations within the RF coil;

rotating one or more standards within the RF coil, acquiring multiple time domain signals for the one or more standards at multiple orientations within the RF coil, and producing an average time domain signal for the one or more standards; and determining the hydrogen content of the sample by comparing the intensity of the average time domain signal for the sample to the intensity of the average time domain signal for the one or more standards.

4. The method of claim 3 wherein the multiple time domain signals have a percent standard deviation and rotating the sample within the RF coil produces a magnitude of about 10 or more reduction in the percent standard deviation.

5. A method for improving the precision of time domain low field H-NMR analysis, the method comprising rotating a sample within a RF coil at a rotation rate of 1° or less per data acquisition window while continuously acquiring multiple time domain signals for the sample at multiple orientations within the RF coil rotating one or more standards within a RF coil, acquiring multiple time domain signals for the one or more standards at multiple orientations within the RF coil, and producing an average time domain signal for the one or more standards; and, determining the hydrogen content of the sample by comparing the intensity of the average time domain signal for the sample to the intensity of the average time domain signal for the one or more standards.

6. The method of claim 5 wherein the rotation rate is 0.1° or less per data acquisition window.

7. The method of claim 5 wherein the rotation rate is 0.01° or less per data acquisition window.

8. The method of claim 5 wherein the multiple time domain signals have a percent standard deviation and rotating the sample within the RF coil produces a magnitude of about 10 or more reduction in the percent standard deviation.

9. A method for improving the precision of time domain low field H-NMR analysis, the method comprising: rotating a sample within a RF coil at a rotation rate of about 15 revolutions per minute while continuously acquiring multiple time domain signals for the sample over data acquisition windows having a duration of about 40 μsecs with a delay of about 25 seconds after acquiring the time domain signal before acquiring a subsequent time domain signal.

10. The method of claim 9 further comprising:

rotating one or more standards within a RF coil, acquiring multiple time domain signals for the one or more standards at multiple orientations within the RF coil, and producing an average time domain signal for the one or more standards; and, determining the hydrogen content of the sample by comparing the intensity of the average time domain signal for the sample to the intensity of the average time domain signal for the one or more standards.

11. The method of claim 10 wherein the multiple time domain signals have a percent standard deviation and rotating the sample within the RF coil produces a magnitude of about 10 or more reduction in the percent standard deviation.

12. The method of claim 9 wherein the multiple time domain signals have a percent standard deviation and rotating the sample within the RF coil produces a magnitude of about 10 or more reduction in the percent standard deviation.

* * * * *